(12) United States Patent
Fassier et al.

(10) Patent No.: US 6,524,313 B1
(45) Date of Patent: Feb. 25, 2003

(54) INTRAMEDULLARY NAIL SYSTEM

(75) Inventors: François Fassier, Montreal (CA);
Pierre Duval, Cowansville (CA); Ariel Dujovne, Côte St. Luc (CA)

(73) Assignee: Pega Medical, St-Leonard (CA)

( * ) Notice: Subject to any disclaimer, the term of this patent is extended or adjusted under 35 U.S.C. 154(b) by 306 days.

(21) Appl. No.: 09/671,164

(22) Filed: Sep. 28, 2000

Related U.S. Application Data

(60) Provisional application No. 60/159,454, filed on Oct. 14, 1999.

(51) Int. Cl.$^7$ .............................................. A61B 17/72
(52) U.S. Cl. ........................................................ 606/63
(58) Field of Search ............................. 606/60, 72, 73, 606/62, 63

(56) References Cited

U.S. PATENT DOCUMENTS

| | | | | |
|---|---|---|---|---|
| 4,016,874 A | * | 4/1977 | Maffei et al. ................. | 606/62 |
| 4,858,602 A | * | 8/1989 | Seidel et al. .................. | 606/60 |
| 5,112,333 A | * | 5/1992 | Fixel ............................ | 606/62 |
| 5,387,239 A | * | 2/1995 | Bianco et al. ............... | 403/118 |
| 5,569,249 A | * | 10/1996 | James et al. .................. | 606/62 |
| 5,704,938 A | * | 1/1998 | Staehlin et al. ............. | 606/105 |
| 5,814,047 A | * | 9/1998 | Emilio et al. ................ | 606/62 |
| 5,961,553 A | * | 10/1999 | Coty et al. .................... | 606/62 |

* cited by examiner

*Primary Examiner*—Eduardo C. Robert
(74) *Attorney, Agent, or Firm*—Ogilvy Renault

(57) ABSTRACT

An intramedullary nail system includes a telescopic nail assembly for use in fixation of long bone fractures. The nail assembly includes a female hollow nail that is attached to the proximal cortex of the femur, and a male solid nail that is attached to the distal cortex. Anchorage of the telescopic nail assembly is achieved through screw type fixation. The intramedullary nail system has a built-in feature that allows for extension of its length as bone structures heal and normal patient growth occurs, which is particularly advantageous to be used for children above two years of age and below 65 kilograms of body weight.

23 Claims, 4 Drawing Sheets

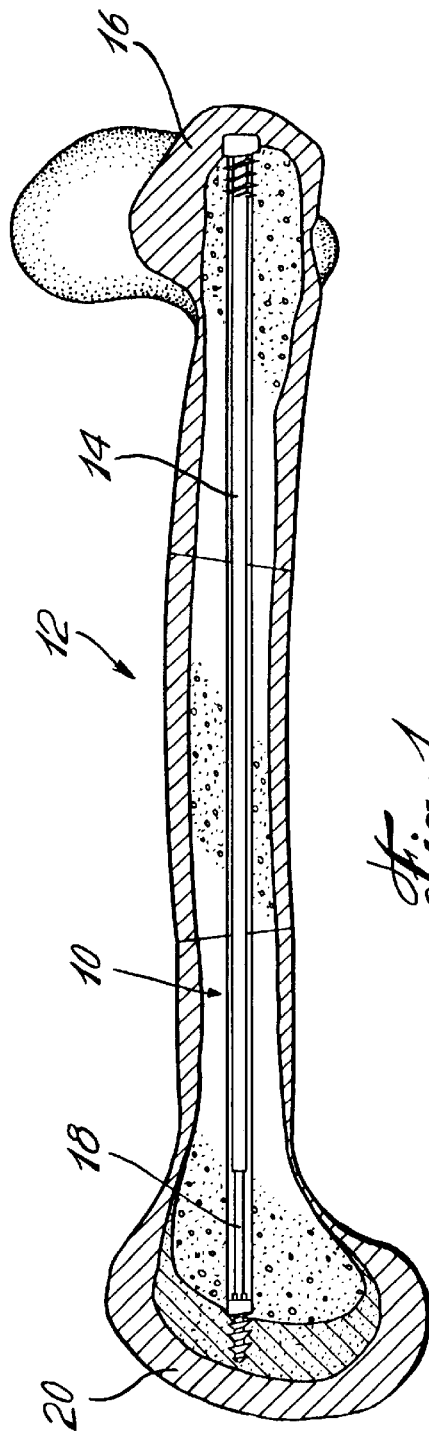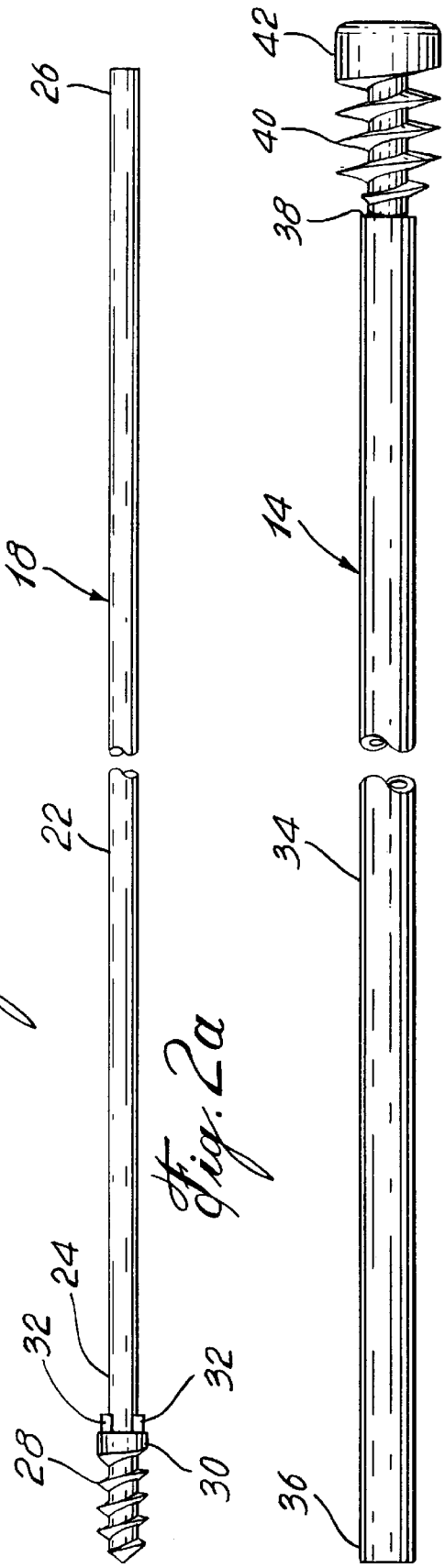

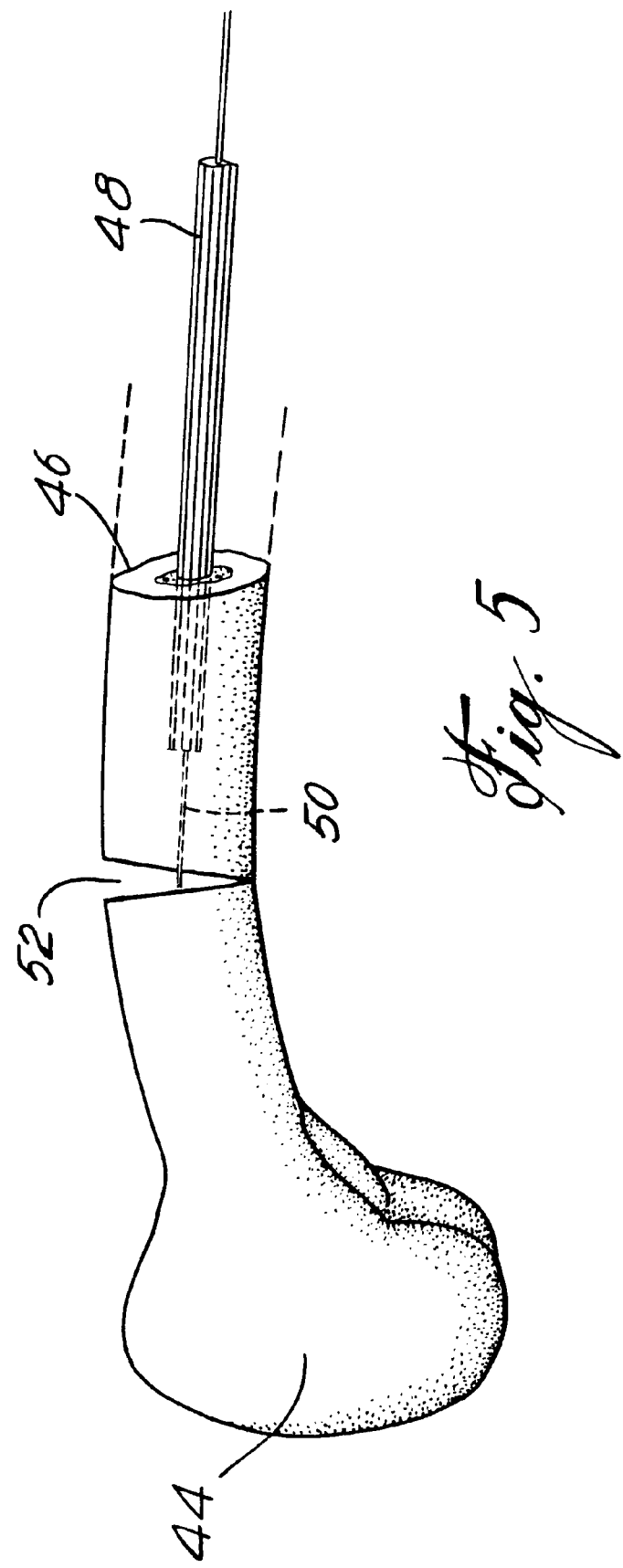

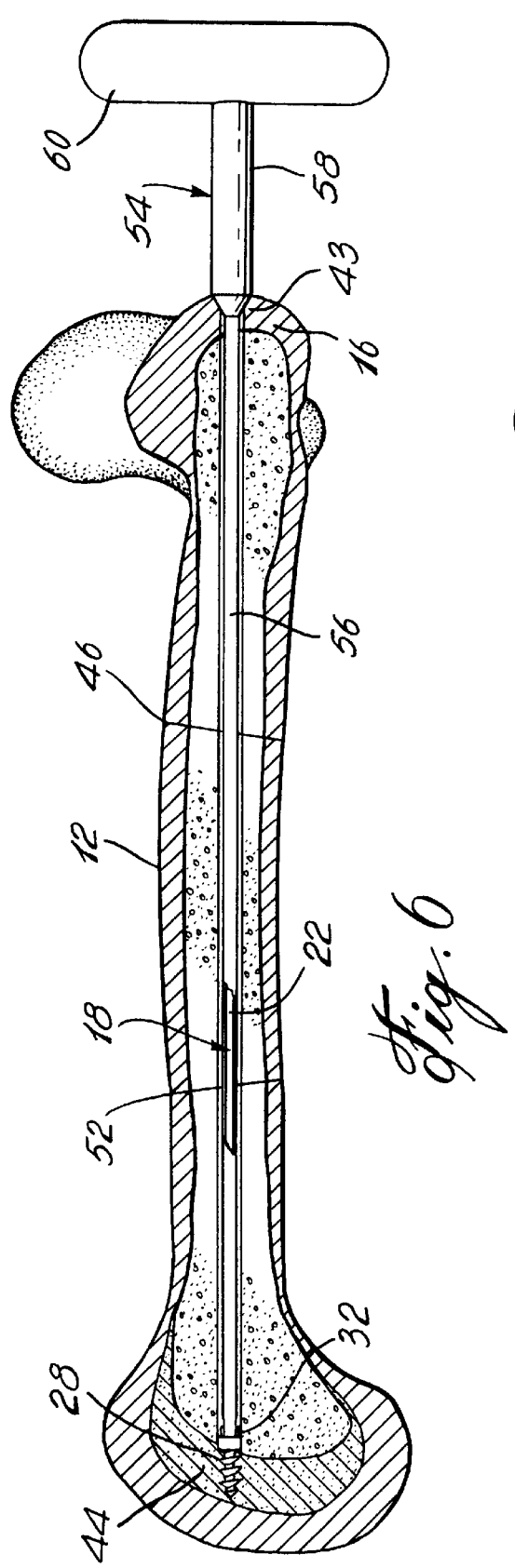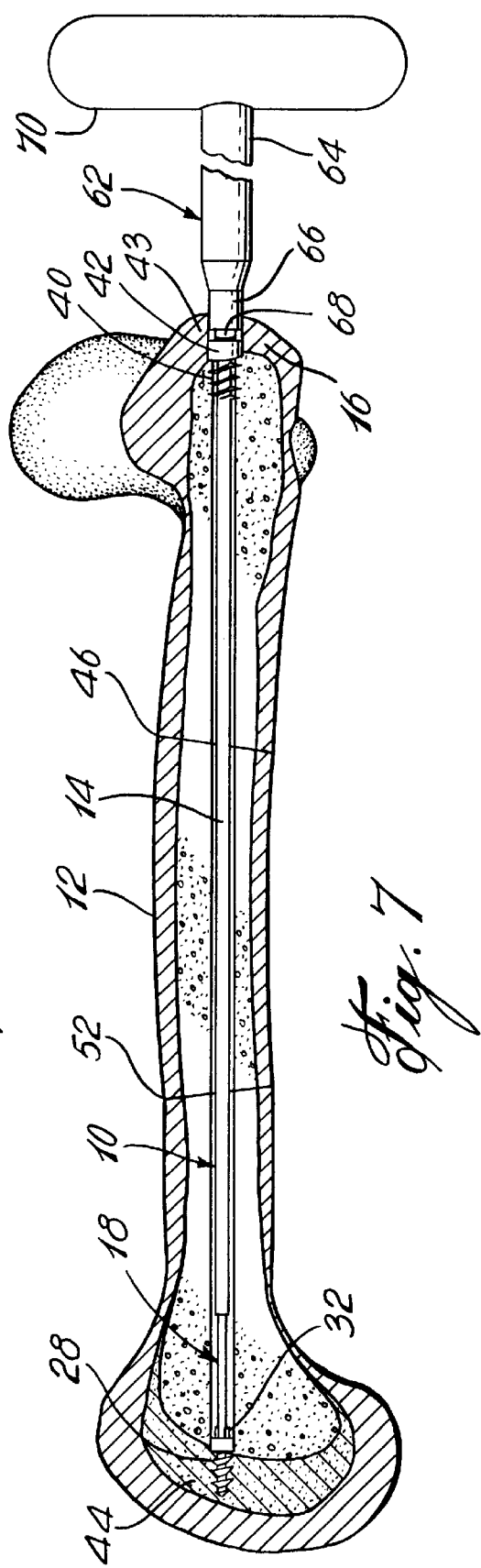

INTRAMEDULLARY NAIL SYSTEM

CROSS-REFERENCE TO RELATED APPLICATION

This application is based on U.S. Provisional Patent Application Ser. No. 60/159,454, filed Oct. 14, 1999.

FIELD OF THE INVENTION

The present invention relates to orthopedic surgical devices, particularly intramedullary nails for surgical placement in a patient's long bone, such as a femur. More particularly, the present invention relates to an improved intramedullary nail assembly that enables the implant to be used in the treatment of children above 2 years of age and below 65 kilograms of body weight.

BACKGROUND OF THE INVENTION

Intramedullary nails have long been used for internal fracture fixation, and have become the preferred implant treatment in many long bone fracture cases. Generally, such a device comprises an extended hollow shaft having a predetermined cross-section and provided with transverse apertures at selected locations along its length. The nail is inserted into an intramedullary canal of a long bone and secured within the bone by transverse bone screws placed through aligned apertures in the nail. The general configuration of intramedullary nails is well illustrated in U.S. Pat. No. 5,935,127, issued to Border on Aug. 10, 1999.

Because the length of the intramedullary nail must be matched to the length of the bone to be repaired, prior art intramedullary nails are produced in a variety of lengths and diameters. In order to limit the number of sizes which must be carried in inventory, recent intramedullary nails have been produced as modular systems having a limited number of base nail members provided in a uniform length and a much larger variety of extension members in varying lengths and diameters. A selected extension member can be joined to any selected base nail member to produce an intramedullary nail of any desired length. One type of modular intramedullary nail system has been disclosed by Engelhardt et al in U.S. Pat. No. 4,805,607. The intramedullary nail of Engelhardt is provided with an extension member available in different lengths and diameters. Another improved type of modular intramedullary nail system has been disclosed in U.S. Pat. No. 5,122,141, issued to Simpson et al on Jun. 16, 1992, which provides a modular intramedullary nail system capable of rotatably receiving a variety of extension members of a selected length, the extension members capable of being secured in any desired angular orientation relative to the base portion of the intramedullary nail.

The modular intramedullary nail systems described in the above two United States patents are advantageous in providing a femoral intramedullary system capable of being adapted to a variety of different length bones, and eliminating a requirement for a precise rotational positioning of the nail prior to insertion of the nail into the intramedullary canal for receiving the transverse bone screws. Nevertheless, the intramedullary nail system is not self-adjustable in length and, therefore, is incapable of providing a surgical fixation to stabilize fractured bones during the healing process without disrupting the normal bone growth particularly of a child patient.

In another example described in U.S. Pat. No. 5,057,103, issued to Davis on Oct. 15, 1991, an adjustable feature is incorporated into a nail that is inserted into the medullary canal of a fractured bone to fixate the bone segments in order to promote healing. The nail provides compressive force to close the fracture and further promote healing. The nail has an outer member and an inner member that is slidable within the outer member. The inner member, at one end, has arms for engaging the interior of the bone cortex in the distal bone segment and, at the other end, a holding member for engaging the cortex in the proximal bone segment. The arms are movable between stowed positions, for allowing insertion of the nail into the bone, and deployed positions for engaging the bone cortex. The force exerted by the arms and the holding member on the bone is adjustable. The adjustable feature essentially provides a mechanism for adjusting the compressive force applied to the bone and does not permit the length of the nail to be adjusted particularly after its implantation.

Prior art located through a diligent search has failed to show references to adjusting solutions for this regard. Therefore, there is a need for an extendable intramedullary nail system for surgical fixation of fracture bones of child patients.

SUMMARY OF THE INVENTION

It is one object of the present invention to provide an intramedullary nail assembly self-extendable in length for surgical fixation of fractured bones of child patients.

It is another object of the present invention to provide an intramedullary nail system for surgical fixation of fractured bones without transverse bone screws.

It is a further object of the present invention to provide an intramedullary nail assembly which can be implanted in a relatively easy method.

Generally, an intramedullary nail assembly for use in fixation of long bone fractures, in accordance with one aspect of the invention, comprises a telescopic rod having two opposed ends and including a female component and a male component telescopically interconnected to permit axial movement of the ends relative to each other; and means for anchoring each end of the telescopic rod to either end of a fractured long bone when the telescopic rod is implanted in the long bone and extends longitudinally through a length of the bone so that the length of the telescoping rod is extendable as the bone heals and normal patient growth occurs.

More especially, according to an embodiment of the present invention, the intramedullary nail assembly is provided with an elongated tube having one end thereof formed with an external thread that preferably has a diameter greater than the external diameter of the tube, and a rod having one end thereof formed with an external thread that is preferably a self-tapping screw with a diameter as large as the external diameter of the tube. The rod is slidably and detachably received in the elongated tube to form the telescoping nail assembly with the threads at opposed ends thereof. The rod is adapted to be separately inserted through the intramedullary canal into the bone until the self-tapping screw is anchored in either end, preferably the distal end of the bone, and the rod spans the fracture. The elongated tube is adapted to be inserted through the canal into the bone to receive the rearward end of the rod sliding into the tube until the external screw at the rearward end of the tube is anchored in the end, preferably the proximal end of the bone. The intramedullary nail assembly, according to the present invention, inhibits radial displacements of the fractured segments of the bone while the nail assembly is axially extendable as bone structures heal and normal patient growth occurs.

The intramedullary nail assembly, according to the present invention, has a unique feature of self-adjustment in length after its implantation to provide a fixation of the fractured bone segments to promote healing without disrupting normal patient growth, which is particularly advantageous when the nail assembly is used for children above two years of age and below 65 kilograms of body weight. Additionally, the nail assembly, according to the present invention, provides a relatively easy method of implantation because there are no transverse bone screws required. The anchorage of the nail assembly is achieved through rotating the respective rod and tube components to let the threads thereon anchor in the bone structures. The rotation of the respective rod end tube is achieved through driving tools detachably connected thereto.

BRIEF DESCRIPTION OF THE DRAWINGS

Having thus generally described the nature of the invention, reference is now to be given to the accompanying drawings by way of examples showing a preferred embodiment, in which:

FIG. 1 is a schematic longitudinal cross-sectional view of a human femur showing the implanted intramedullary nail assembly of the present invention in accordance with a preferred embodiment;

FIG. 2a is a side view of a male nail of the intramedullary nail assembly shown in FIG. 1;

FIG. 2b is a side view of a female nail of the intramedullary nail assembly shown in FIG. 1;

FIG. 5 is a schematical perspective view of a distal fragment of the bone, showing the reaming of the fragment with a female reamer;

FIG. 6 is a schematic longitudinal cross-sectional view of the bone, showing the male nail as anchored in the bone using the male driving tool; and FIG. 7 is a schematic longitudinal cross-sectional view of the bone showing the female nail sliding over the male nail and anchored in the bone using a female driving tool.

DETAILED DESCRIPTION OF THE EMBODIMENTS

Figures 3, 4:
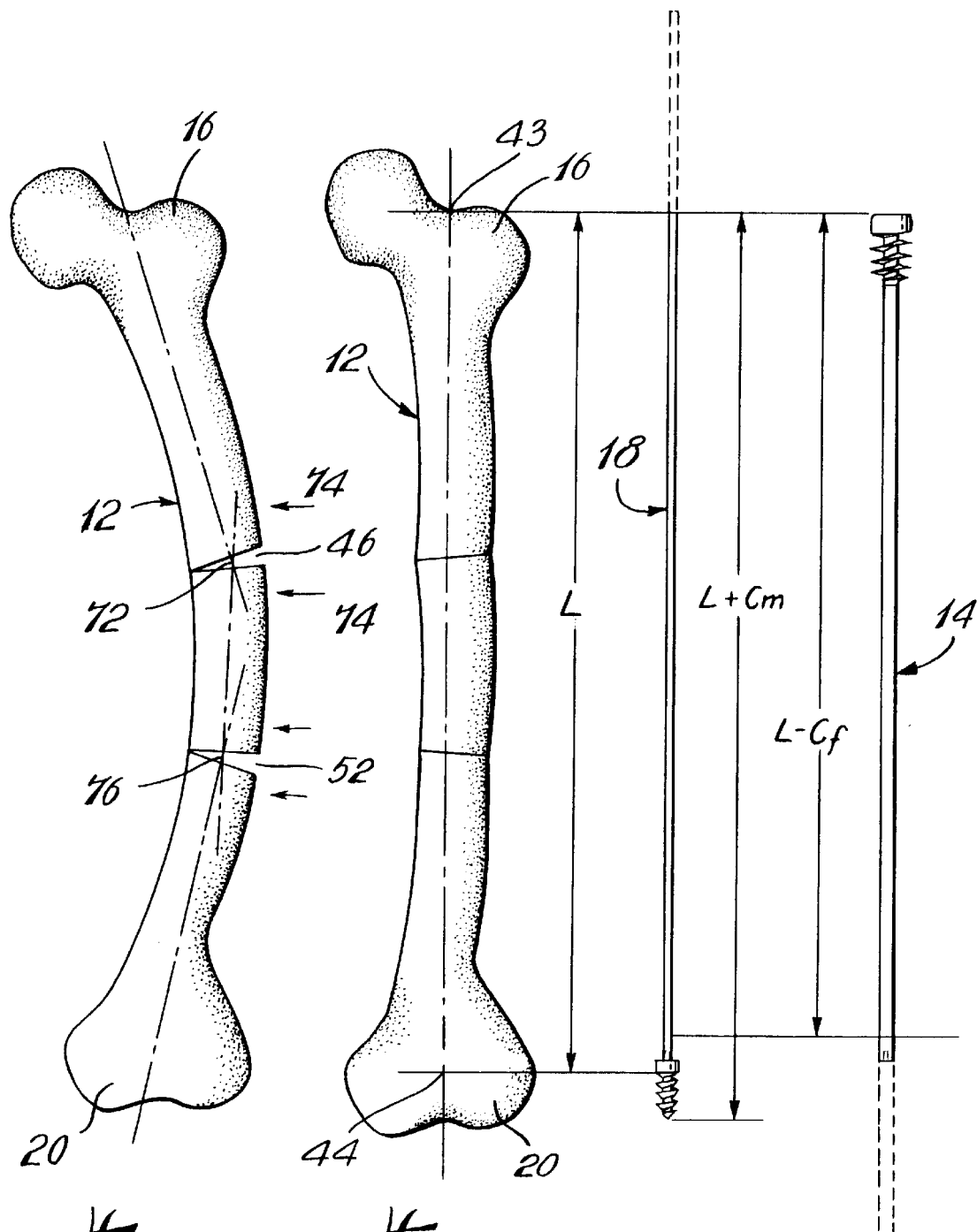
FIG. 3 is a schematic side view of a human femur which is fractured before being rectified.
FIG. 4 is a schematic side view of the human femur shown in FIG. 3, and the male and female nails in preparation, showing the length of the rectified bone after osteotomies and its relation relative to the respective length of the male and female nails.

In FIG. 1 there is a intramedullary nail assembly generally indicated by numeral 10 which is a telescopic rod for use in fixation of long bone fractures, and implanted in a human femur 12. The intramedullary nail assembly includes a female hollow nail 14 which is attached to the proximal end, trochanteric cortex 16 of the femur 12 and a male solid nail 18 which is attached to the distal end, knee cortex 20 of the femur 12. Anchorage of the nail assembly 10 is achieved through screw type fixation and will be described further with reference to FIGS. 2a and 2b. The nail has a built-in feature that allows for extension of its length as the bone structures heal and normal patient growth occurs.

FIGS. 2a and 2b illustrate the respective male solid nail 18 and the female hollow nail 14. The male solid nail 18 includes a solid rod 22 having a forward end 24 and a rearward end 26. A self-tapping screw 28 is formed at the forward end 24 of the rod 22. The self-tapping screw 28 has a diameter gradually increasing from its tip to a guiding shoulder 30 which has a diameter as large as the internal diameter of the female hollow nail 14. A pair of keys 32 is provided, diametrically opposed on the rod 22 at the forward end 24 adjacent to the guiding shoulder 30. The female hollow nail 14 includes an elongated tube 34 having the internal diameter adequate to receive the rod 22 sliding thereinto. The elongated tube 34 includes a forward end 36 and a rearward end 38. An external thread 40 with an unthreaded end portion 42 is formed at the rearward end 38 of the tube 34. The unthreaded end portion 42 has an external diameter greater than the external diameter of the tube 34 and a hexagonal socket is defined within the unthreaded end portion 42 (not shown). The diameter of the external thread 40 gradually increases rearwards to a diameter as large as the external diameter of the unthreaded end portion 42.

The intramedullary nail assembly 10 is manufactured in both Ti alloy (Ti6A14V ASTM-136) and medical grade Stainless Steel (316L, ASTM138). The intramedullary nail assembly 10 is manufactured in 5 diameters: 3.2, 4.0, 4.8, 5.6 and 6.0 mm and each 300 mm in length.

FIG. 3 shows the fractured bone 12 before it is rectified, and FIG. 4 shows the rectified bone 12 after osteotomies. L is the distance between the ossified greater trochanter 43 and the distal epiphysis 44. In preparation of the nail assembly 10 for the fixation of the fractured bone 12, the length of the female hollow nail 14 should be the distance L minus the coefficient $C_f$, and the length of the male solid nail 18 should be equal to the distance L plus the coefficient $C_m$. Those coefficients $C_f$ and $C_m$ vary with nail size. For example, $C_f$ is 7 mm, unchanged for the nail assembly sizes 3.2, 4.0, and 4.8 mm, while $C_m$ is 10, 15 and 20 mm for those nail assemblies. If L is calculated at 200 mm for a type 3.2 nail assembly, for example, then the nail length is 210 mm (L plus $C_m$) and the female length will be 193 mm (L minus $C_f$). However, the length L of the rectified bone after osteotomies is not measurable before the bone is rectified, as shown in FIG. 3. Therefore, the length L should be estimated before the surgical operation. It is noted that a 10% magnification must be taken into account when measuring L from an X-ray.

Standard surgical technique for the placement of the nail assembly 10 is recommended. The surgical technique manual should be carefully followed.

In a surgical implantation of the nail assembly 10, the standard technique usually employed is the open osteotomy technique which is well known. The operation begins with a classic postero-lateral approach. The femur 12 is exposed sub-periostally, and then the first osteotomy which is indicated by numeral 46 in FIG. 3 is executed through a first incision on the C-arm guidance (not shown). The intramedullary canal of the fragments of the femur 12 should be reamed using a reamer having a diameter as large as the diameter of the nail assembly to facilitate insertion of the respective male solid nail 18 and the female hollow nail 14. The reamer 48 as shown in FIG. 5 includes a male K-wire 50 for guidance. The reaming of the proximal and distal fragments is done through the first osteotomy 46. The reaming of the proximal fragment is up to the greater trochanter 43 over the male K-wire guide 50. When the same preparation of the distal fragment is conducted and if the K-wire guide 50 does not reach the distal epiphysis 44, a second osteotomy 52 should be performed after reaming the intermediate fragment. The second osteotomy 52, if necessary, will be done at the extremity of the reamer perforation. In such a case, a larger incision or a more distal incision will be inevitable for the second osteotomy. Afterwards, the most distal fragment should be reamed down to the epiphysis 44.

The male solid nail 18 is inserted in the retrograde direction from the osteotomy through the proximal fragments. In case a second osteotomy, such as osteotomy 52, is needed, the male solid nail 18 is inserted from the distal osteotomy 52. A second incision will be done at the buttock of the patient to allow the rearward end 26 of the male nail 18 to exit proximally. A male driver 54 is then inserted over the rod 22, as shown in FIG. 6, through the buttock incision (not shown), and the male solid nail 18 is pushed distally after reduction of the osteotomies 46 and 52, and screwed into the distal epiphysis 44. The male driver 54 includes an elongated tube 56 that has an internal diameter greater than the external diameter of the rod 22 of the male nail 18 for sliding over the rod 22 and has an external diameter smaller than the diameter of the nail assembly so that it can be freely rotated in the reamed longitudinal passage. The elongated tube 56 is formed with a transverse groove at the forward end thereof (not shown) for detachably engaging the keys 32 on the male solid nail 18 to rotate the nail 18 to anchor the screw 28 in the bone. A cylindrical base portion 58 is extended from a rearward end of the tube 56 and connected to a handle 60 which is used for receiving a torque manually applied to the driver 54.

The female hollow nail 14 is inserted through the buttock incision over the male solid nail 18 after the male solid nail 18 is screwed in the distal epiphysis 44 and the male driver 55 is removed. A female driver 62 is used to rotate the female hollow nail 14 until the female hollow nail 14 is screwed proximally in the greater trochanter 43 and flush to the cartilage/bone surface, as shown in FIG. 7. The female driver 62 includes an elongated cylindrical body 64 having a forward end portion 66 that has a diameter as large as the diameter of the unthreaded end portion 42 of the female hollow nail 14. A hexagonal key 68 protrudes axially from the forward end portion 66 for detachably engaging the hexagonal socket in the unthreaded end portion 42 of the female hollow nail 14 to apply a torque thereto. The elongated cylindrical body 64 is attached at its rearward end to a handle 70 for receiving a torque to be applied to the female hollow nail 14. The surgical operation is completed after the female driver 62 is removed and all incisions are closed.

For patients with larger bones and thin cortices, the use of the percutaneous technique, also well known, is recommended. The surgical operation begins with the reaming of the intramedullary canal of the bone with the reamer tool 48. The femur 12 is reamed to the appropriate size (3.2, 4.0, or 4.8 mm) depending on the selected size of the nail assembly 10. With reference to FIG. 3 the reamer tool 48 (not shown in FIG. 3) is inserted through the buttock incision (not shown) and the greater trochanter 43 into the intramedullary canal (not shown in FIG. 3) of the femur 12 until the K-wire guide 50, as shown in FIG. 5, reaches the apex of the deformity as indicated at numeral 72. The male solid nail 18 guided with the male driver 54 which is over the rod 22 of the male nail 18, as shown in FIG. 6, is inserted through the buttock incision and the greater trochanter into the perforation until the self-tapping screw 28 is positioned close to the deformity 72. The first osteotomy 46 is down through a 0.5 cm incision (not shown) in the convexity of the deformity 72. With counter-pressure indicated by arrows 74 applied at the osteotomy side (with a hammer, for example), the deformity 72 is progressively corrected (osteoclasis) by gentle manipulation. When the bone is straightened, the male solid nail 18 guided with the male driver 54 is pushed distally past the osteotomy 46.

The male solid nail 18 is rotated and pushed with the male driver 54 to the apex of the second deformity 76. Then, the second osteotomy 52 should be done at the extremity of the male solid nail 18, following the same procedure described above for straightening the bone at the deformity 72. After the deformity 76 is corrected, the remaining steps of the operation should follow the same procedure described above with reference to FIGS. 6 and 7 regarding the open osteotomy technique.

It is noted that the intramedullary nail assembly 10 can be attached to bony structures without disrupting the bone growth plate. Neither the hip nor the knee articulation is interrupted during implantation.

The intended use of the intramedullary nail assembly, according to the invention, is as a temporary implant to aid in the healing of long diaphysis fractures in order to prevent further fractures in patients with Osteogenesis Imperfecta. It is particularly intended for children above two years of age and below 65 kilograms of body weight. However, it is apparent that the nail assembly according to the invention can also be used for adult patients or animals.

The above description is intended for illustrative purposes only and is not intended to limit the scope of the present invention in any way. Changes and modifications to the embodiment of the invention described above may be made without departing from the spirit and scope of the invention which are intended to be limited only by the scope of the appended claims.

We claim:

1. An intramedullary nail assembly for use in fixation of long bone fractures comprising:
    a telescopic rod having two opposed ends and including a female component and a male component telescopingly interconnected to permit axial movement of the ends relative to each other; and
    means for anchoring each end of the telescopic rod to either end of a fractured long bone when the telescopic rod is implanted in the long bone and extends longitudinally through a length of the bone so that the length of the telescopic rod is extendable as the bone heals and bone growth occurs.

2. The intramedullary nail assembly as claimed in claim 1, wherein the anchoring means comprises a thread fastening mechanism at each end of the telescopic rod.

3. The intramedullary nail assembly as claimed in claim 2, wherein the male component comprises a self-tapping screw fixed on the male component forming one of the opposed ends of the telescopic rod and the female component comprises an external thread fixed on the female component forming the other end of the telescopic rod.

4. The intramedullary nail assembly as claimed in claim 3, wherein the male component is detachable from the female component so that the male component is adapted to be implanted in the bone and anchored in one end of the bone using the self-tapping screw before the female component is implanted.

5. The intramedullary nail assembly as claimed in claim 1, wherein each of the male and female components has a length thereof such that the nail assembly is adapted to be attached to bony structures without disrupting a bone growth plate.

6. An intramedullary nail assembly for use in fixation of long bone fractures comprising:
    an elongated tube having one end thereof formed with a bone engagement means;
    a rod having one end thereof formed with a bone engagement means;

the rod being slidably and detachably received in the elongated tube to form a telescopic nail assembly with the bone engagement means at opposed ends thereof; and whereby the telescopic nail assembly is adapted to be implanted in a fractured long bone, extending longitudinally through a length of the bone with the bone engagement means at each end of the telescopic nail assembly anchored in either end of the bone and being extendable as the bone heals and bone growth occurs.

7. The intramedullary nail assembly as claimed in claim 6, wherein the bone engagement means is an external thread.

8. The intramedullary nail assembly as claimed in claim 7, wherein the thread formed at the end of the rod is a self-tapping screw.

9. The intramedullary nail assembly as claimed in claim 8, wherein the self-tapping screw has a diameter as large as an external diameter of the elongated tube.

10. The intramedullary nail assembly as claimed in claim 8, wherein the rod includes a connector located close to the self-tapping screw so that a driving tool is enabled to detachably connect the connector to apply a torque to the rod for anchoring the self-tapping screw in the bone.

11. The intramedullary nail assembly as claimed in claim 7, wherein the thread at the end of the tube has a diameter larger than an external diameter of the elongated tube.

12. The intramedullary nail assembly as claimed in claim 7, wherein the elongated tube includes a connector located close to the external thread so that a driving tool is enabled to detachably connect the connector to apply a torque to the tube for anchoring the external thread in the bone.

13. The intramedullary nail assembly as claimed in claim 6, wherein the nail assembly is made from Ti alloy.

14. The intramedullary nail assembly as claimed in claim 6, wherein the nail assembly is made from medical grade stainless steel.

15. A method of treating a fracture in a long bone having an intramedullary canal comprising steps of:

inserting a male nail having a rod and a first bone engagement portion at a forward end of the rod through the intramedullary canal into the bone until the first bone engagement portion is anchored in either one end of the bone, with the rod spanning the fracture;

inserting a female nail having an elongated tube and a second bone engagement portion at a rearward end of the tube through the canal into the bone, to receive a rearward end of the rod sliding into the tube until the second bone engagement portion is anchored in an end of the bone opposite to the end where the first bone engagement portion is anchored so that the male and female nails are axially extendable relative to each other when bone structures heal and bone growth occurs.

16. The method as claimed in claim 15, wherein the first bone engagement portion is a self-tapping screw anchored in a distal epiphysis of the bone and the second bone engagement portion of the female nail is anchored in a greater trochanter.

17. The method as claimed in claim 16, wherein the second bone engagement portion of the female nail is anchored in a place beyond a growth plate of bony structures.

18. The method as claimed in claim 17, wherein the male and female nails are inserted through the greater trochanter of the bone respectively.

19. The method as claimed in claim 17, wherein the male nail is inserted through a postero-lateral approach.

20. The method as claimed in claim 16, wherein the self-tapping screw has a diameter as large as an external diameter of the tube to facilitate the insertion of the female nail.

21. The method as claimed in claim 16, comprising a step of using a driving tool detachably connected to a connector on the rod located close to the self-tapping screw to apply a torque to the male nail to anchor the self-tapping screw in the bone.

22. The method as claimed in claim 16, comprising a step of using a driving tool detachably connected to a connector at the rearward end of the tube to apply a torque to the female nail to anchor the external thread in the bone.

23. The method as claimed in claim 15, comprising a step of reaming at least a portion of the intramedullary canal before the insertion of the male nail to facilitate the insertion.

\* \* \* \* \*